United States Patent [19]

Buysch et al.

US005717127A

[11] Patent Number: 5,717,127

[45] Date of Patent: Feb. 10, 1998

[54] PROCESS FOR PREPARING 6-OXO-(6H)-DIBENZ-[C,E] [1,2]-OXAPHOSPHORINS

[75] Inventors: Hans-Josef Buysch; Volker Glock, both of Krefeld, Germany

[73] Assignee: Bayer Aktiengesellschaft, Leverkusen, Germany

[21] Appl. No.: 633,609

[22] Filed: Apr. 17, 1996

[30] Foreign Application Priority Data

Apr. 24, 1995 [DE] Germany ............... 195 14 946.7

[51] Int. Cl.⁶ ............................................. C07F 9/6574
[52] U.S. Cl. .................................................... 558/82
[58] Field of Search ...................................... 558/82

[56] References Cited

U.S. PATENT DOCUMENTS 4,086,206  4/1978  Saito et al.
5,481,017  1/1996  Kleiner.

FOREIGN PATENT DOCUMENTS 0632050  1/1995  European Pat. Off.
2034887  1/1972  Germany.
2730371  1/1978  Germany.

OTHER PUBLICATIONS

Chemical Abstracts, vol. 76, abstract No. 99823z, p. 471, abstract of DE 2,034,887, (1972).

Primary Examiner—Johann Richter
Assistant Examiner—Michael G. Ambrose
Attorney, Agent, or Firm—Sprung Horn Krammer & Woods

[57] ABSTRACT

For the continuous preparation of 6-oxo-(6H)-dibenz-[c,e][1,2]-oxaphosphorins (ODOPs), 6-chloro-(6H)-dibenz-[c,e][1,2]-oxaphosphorins (CDOPs) are continuously reacted with at least the stochiometrically required amount of water at elevated temperature in a reaction section having little backmixing.

15 Claims, 3 Drawing Sheets

Fig. 1a-c

PROCESS FOR PREPARING 6-OXO-(6H)-DIBENZ-[C,E] [1,2]-OXAPHOSPHORINS

BACKGROUND OF THE INVENTION

1. Field of the Invention

The invention relates to a process for the continuous preparation of 6-oxo-(6H)-dibenz-[c,e][1,2]-oxaphosphorins (ODOPs) by reaction of 6-chloro-(6H)-dibenz-[c,e][1,2]-oxaphosphorins (CDOPs) with at least the stochiometrically required amount of water by continuous reaction of CDOP and water at elevated temperature in a reaction section having little backmixing and optionally treatment of the ODOP at elevated temperature. CDOP is here prepared in an upstream 1st reaction stage by reaction of o-phenylphenols with $PCl_3$.

ODOPs are important additives for polymers for protection against oxidative degradation and for flame-proofing and further serve as starting materials for preparing further polymer additives.

2. Description of the Related Art

German Offenlegungsschrift 20 34 887, Examples 5 and 6, discloses the preparation of 6-oxo-(6H)-dibenz-[c,e][1,2]-oxaphosphorins (ODOPs) by alkaline hydrolysis of 6-chloro-(6H)-dibenz-[c,e][1,2]-oxaphosphorins with soda solution. In a cumbersome operation, this gives first the sodium salt of hydroxyphenylphenylphosphinic acid (III) in strongly contaminated aqueous-alkaline solution which has to be purified by means of activated carbon:

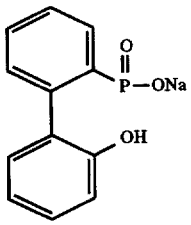

The sodium salt (III) is convened by acidification into the free acid. This can, since it is sparingly soluble, be isolated from the aqueous salt solution. Subsequently, it has to be converted into the desired ODOP by heating to relatively high temperatures in vacuo. This is a very complicated and relatively environmentally unfriendly process, since it is associated with formation of salts and large amounts of wastewater.

Another reference (German Offenlegungsschrift 27 30 371, pp. 18 and 19) describes that 6-chloro-(6H)-dibenz-oxaphosphorin at 130° C. is combined with a large amount of water, the hydrolysis is carried out, the water is distilled off under reduced pressure and the 6-oxo-dibenzoxaphosphorin is then obtained. The operation described is technically very problematical and can hardly be carried out on a large scale, since water vaporizes at 130° C. and cools the reaction mixture. It is therefore necessary to work under elevated pressure if the temperature of 130° C. is to be maintained and thus uncontrolled crystallization is to be prevented, since the target compound melts significantly above the boiling point of water.

According to a further example (Example 3 in German Offenlegungsschrift 20 34 887), a crude product from the esterification of an o-phenylphenol with $PCl_3$ is hydrolysed by pouring onto ice. This gives the corresponding phosphinic acid which has to be separated from the water and, in a separate process step, converted into the corresponding oxaphosphorin.

The processes mentioned give, as by-products of the oxaphosphorin synthesis, dilute and contaminated hydrochloric acid as a by-product which is difficult to use and to dispose of as well as salt solutions and wastewater.

None of the processes described for preparing ODOP makes any statements about the yield and the purity of the product. In each case it is merely observed that the desired product has been obtained.

An improvement proposed in EP 632 050 is to set the molar ratio of CDOP to water to exactly 1:1 and in this way to avoid large amounts of wastewater. Although this process gives very good yields, the product quality in respect of the residual chlorine content leaves something to be desired—this is particularly important because chlorine residues can cause corrosion and discoloration—and the reaction and hence occupation times of the reaction vessels become long and costly with increasing batch size.

SUMMARY OF THE INVENTION

It has now been found that these disadvantages are overcome if the hydrolysis is carried out at elevated temperature in a continuously operating reactor system having very little backmixing. This gives extremely low chlorine contents and short reaction times.

The present invention provides a process for preparing 6-oxo-(6H)-dibenz-[c,e][1,2]-oxaphosphorins (ODOPs) of the formula

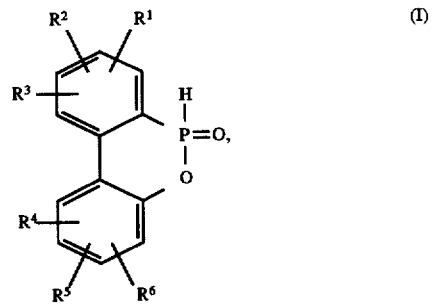

where
$R^1$ to $R^6$ are identical or different and are hydrogen, halogen, $C_1$–$C_4$-alkyl or $C_1$–$C_4$-alkoxy,
by reaction of o-phenylphenols of the formula

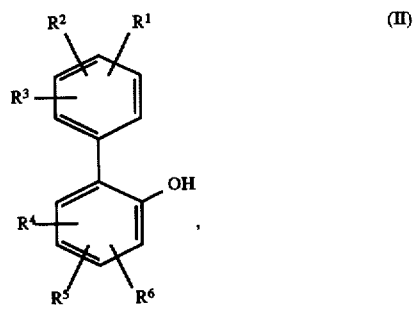

where
$R^1$ to $R^6$ are as defined above,
with phosphorus trichloride in the presence of Lewis acids with elimination of hydrogenchloride at elevated temperature in the range from 70° to 220° C. in a 1st stage and hydrolysis of the product of the 1st stage in a 2nd stage, which is characterized in that, for the purposes of the hydrolysis, CDOP and water in an at least stoichiometric molar ratio are fed continuously at elevated temperature into a reaction section having very little backmixing, the hydrolysis is carried out continuously along this reaction section at elevated temperature, the reaction products are discharged continuously at the end of the section and ODOP is optionally subjected to further treatment at elevated temperature.

BRIEF DESCRIPTION OF THE DRAWINGS

The accompanying drawings (FIGS. 1a–c, 2a–c and 3) show reactor designs for embodiments of the inventive process.

DETAILED DESCRIPTION OF THE INVENTION

Figure 1:
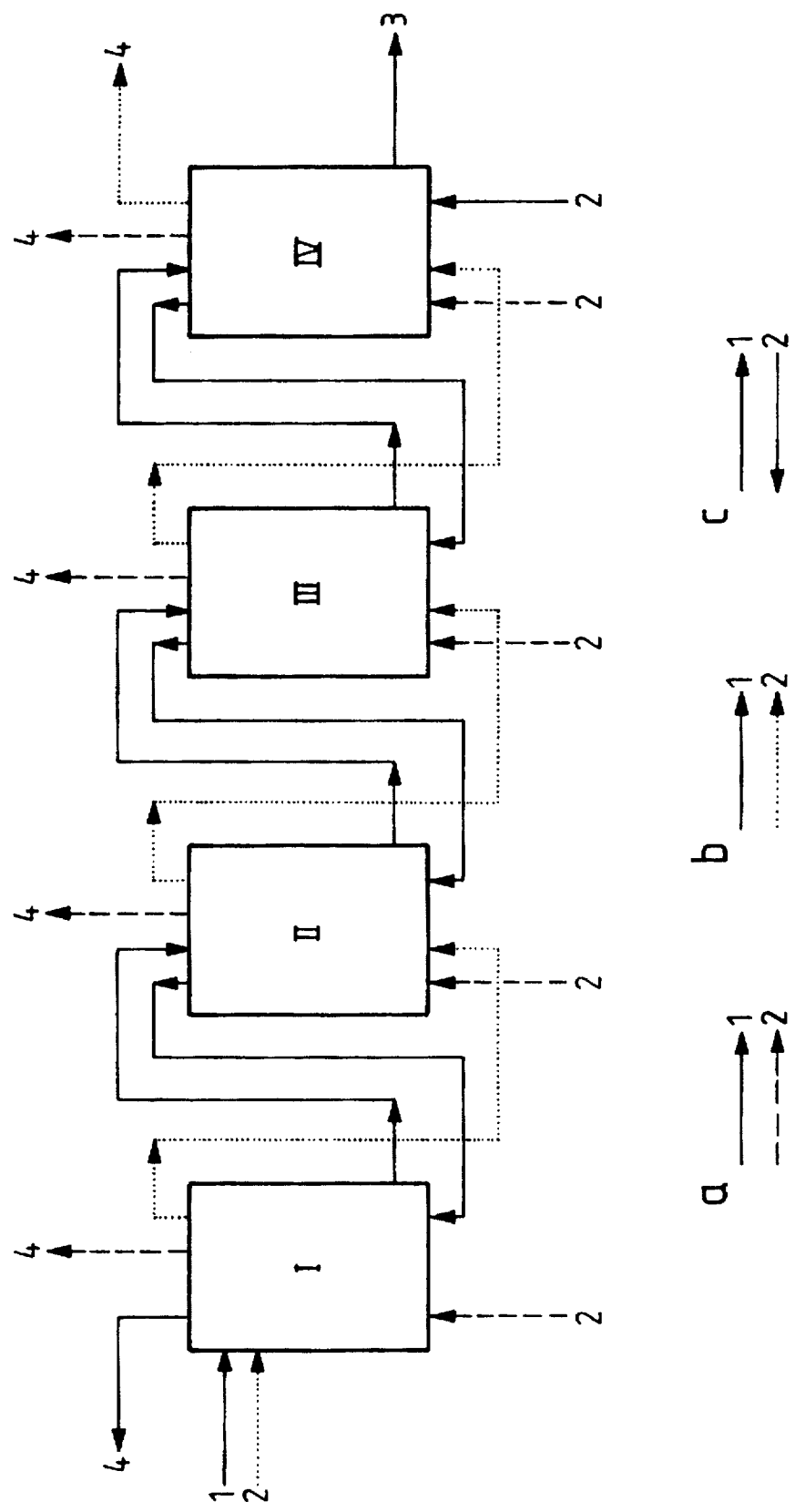

Preference is given to using o-phenylphenols in which two of the radicals $R^1$ to $R^6$ are hydrogen; particularly preferably, four of the radicals $R^1$ to $R^6$ are hydrogen; very particularly preference is given to unsubstituted o-phenylphenol. In each case in (II), hydrogen is present in at least one of the positions on the non-OH-substituted benzene ring which are necessary for formation of the oxaphosphorin ring.

The amount of water used for the hydrolysis has to be at least equivalent to the amount of CDOP used, preference is given to additionally using a small excess of up to 1 mol of $H_2O$, particularly preferably up to 0.7 mol, very particularly preferably up to 0.5 mol of $H_2O$, per mol of CDOP. The total amount of $H_2O$ is accordingly 1–2 mol, preferably 1–1.7 mol, particularly preferably 1–1.5 mol, per mol of CDOP.

The reaction can be carried out in the presence of a solvent. Suitable solvents are, for example, aliphatic and aromatic hydrocarbons having 6–15 carbon atoms and being able to bear 1 or 2 halogen atoms, for example methylcyclohexane, isooctane, isodecane, isododecane, isononane, dimethylcyclohexane, benzines such as petroleum ether, dicyclopentane, decalin, toluene, xylenes, cumene, mesitylene, cymenes, chlorobenzene, chlorotoluene, bromobenzene, dichlorobenzene, chlorocumene, ethylbenzene, diethylbenzene and mixtures of these compounds. However, it is also possible to carry out the hydrolysis in the absence of a solvent, i.e. using a CDOP melt.

The temperatures in the hydrolysis are from 60° to 250° C., preferably from 80° to 230° C., particularly preferably from 100 to 220° C., very particularly preferably from 130° to 210° C. The hydrolysis temperature can be kept constant, but is preferably increased continuously or in stages as the hydrolysis progresses.

The pressure is not particularly critical and in both stages, but independently of one another, is from 0.5 to 50 bar, preferably from 0.6 to 40 bar, particularly preferably from 0.8 to 30 bar.

The continuous hydrolysis is generally carried out by feeding CDOP and water in the desired molar ratio continuously into a reactor system which allows no or at most only partial backmixing and ensures good mixing of CDOP and water.

Such a reactor can be, for example, a cascade of at least 2, preferably from 3 to 5, stirred vessels, into which water in the calculated amounts is fed separately and transversely into each vessel, while CDOP flows, with formation of ODOP, as main stream through the entire cascade after introduction into the first vessel, but HCl formed leaves each vessel separately (FIG. 1a). However, it is also possible to introduce CDOP into the first vessel and send the water required towards it in countercurrent from the last vessel, and to take HCl formed from the first vessel and ODOP from the last vessel (FIG. 1c). However, water and CDOP can also be introduced into the first vessel in cocurrent and after reaction be taken from the last vessel as HCl or ODOP stream (FIG. 1b).

A particularly simple way of carrying out the continuous hydrolysis is in tubular reactors, for example in bubble columns, of which at least 2, preferably 3 to 6, are arranged in a cascade. In this case, the same methods of operation as for the cascade of stirred vessels is possible, i.e. countercurrent mode, cocurrent mode and separate transverse metering-in of water into each bubble column (FIG. 1a–c). The bubble columns can also be arranged vertically above one another as cascaded bubble columns connected to one another in such a way that liquid and gas phase can flow from one sub-bubble column to the next (FIG. 2a). Here too, it is possible to use the various modes of operation, but a particularly simple way is the countercurrent mode where CDOP is introduced at the top and water is introduced at the bottom of the cascaded bubble column. However, the metering-in of water can be distributed to various metering points along the chain of the cascaded bubble columns according to the existing degree of hydrolysis and the water requirement determined therefrom.

A further preferred embodiment of the invention comprises carrying out the hydrolysis in a column apparatus as is customarily used for distillative separation operations. For the purpose of this invention, these are, for example, columns having fixed internal fittings. Suitable apparatus are generally tray columns, e.g. those having sieve, bubble cap, valve, tunnel or centrifugal trays, which in turn can be present in different configurations (FIG. 2b). However, the columns can also contain packing elements and ordered packings. The packing elements or ordered packings to be used are those which are customary per se for distillations, as are described, for example, in Ullmann's Encyclopädie der Technischen Chemie, 4th edition, Volume 2, p. 528 ff. or in the literature of the relevant apparatus manufacturers. Examples which may be mentioned are: Raschig or Pall rings, Berl, Intalex or Toms saddles, Interpack elements of various materials such as glass, stoneware, porcelain, stainless steel, plastic, which can, particularly when metal is used, be in woven or knitted form. Preference is given to packing elements and ordered packings having a large surface area, good wetting and sufficient residence times of the liquid phase; these are, for example, Pall and Novolax rings, Bed saddles, BX packings, Montz-Pak, Mellapak, Kerapak and CY packings. In these embodiments in a reaction column (FIG. 2c) too, the various modes of operation, viz. cocurrent mode, countercurrent mode and the distributed transverse metering in of water, can be used. However, preference is given to the countercurrent mode and the method using distributed metering in of water corresponding to the need at various points on the column.

A further preferred embodiment of the process of the invention is the use of simple tube reactors (FIG. 3) in which static mixing elements ensure good mixing of CDOP and water. Such mixing elements are described, for example, in Ullmann's Encyclopädie, 5th Ed., Vol. B2: pp. 25-12 and 26-9 and Vol. B4: pp. 568–570. In such tube reactors, a minimum flow rate has to prevail so that mixing of the starting materials can be effected. The data required can easily be determined by those skilled in the art. The tube reactors can be operated either in a vertical or horizontal position or in wound form, for example in coil, worm or helical form. Here too, water can be metered in at various points of the tube according to need.

At atmospheric or superatmospheric pressure, reactors which are vertical or have a coil, worm or helical configuration are preferably operated by feeding the starting materials in at the lower end of the reactor and taking off the products at the upper end. However, the reactors can also be operated in the reverse direction from the top downwards. The reaction is preferably carried out under a gauge pressure of from 0.5 to 20 bar. When the process is carded out under pressure, the reaction mixture is continuously depressurized into a container and HCl is separated from ADOP which flows away at the bottom of the depressurization vessel, while HCl is taken off at the top via a cooling facility (FIG. 3).

In all cases described, it is convenient and advantageous to subject the finished reaction mixture after separating off HCl to a further treatment at relatively high temperature. An apparatus for this purpose can be, for example, a stirred vessel, a bubble column, a reaction column or a simple tube having mixing elements. Such apparatus can be separate from the continuous hydrolysis facilities or else be integrated into the latter. Thus, for example, the last vessel or the last bubble column of a cascade can perform this task. Elevated temperature is the range up to the abovementioned upper limit, for example the range 130°–250° C., preferably 150°–180° C. In column reactors, this operation is conveniently carried out in the lower part and the temperature there is increased, as is indicated, for example, in FIG. 2. The temperature ranges specified there are not binding, but are merely indicated as possible. The same applies to the temperature values and the use associated therewith of the last section of the tube in FIG. 3.

Figure 2:
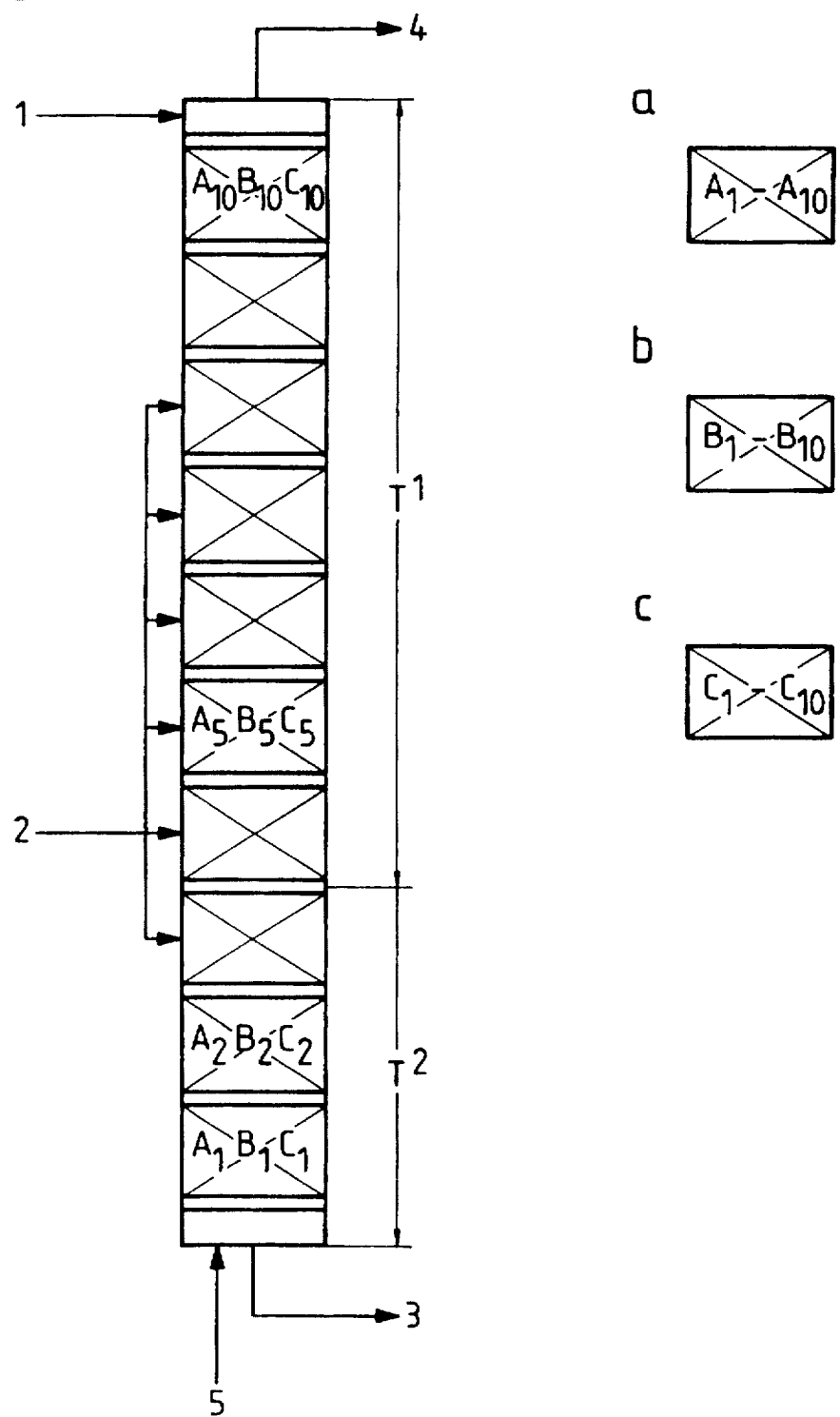
Figure 3:
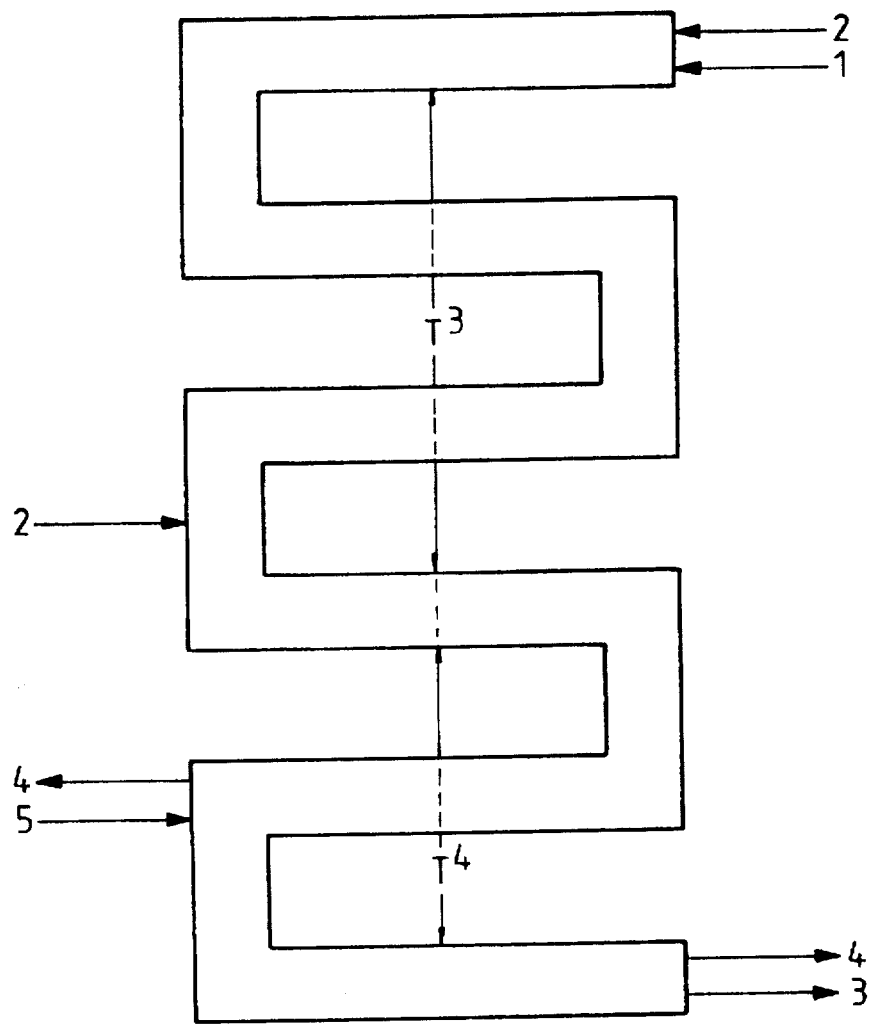

The concomitant use of an inert gas is often advantageous and likewise shown by way of example in FIGS. 2 and 3. Inert gases are, for example, nitrogen, carbon dioxide, helium, hydrogen, methane and other low-boiling hydrocarbons.

In FIGS. 1a–c, 2a–c and 3, the reference numerals refer to material streams or apparatus parts, with the same numerals always having the same meaning: 1=CDOP; 2=$H_2O$; 3=ODOP; 4=HCl; 5=inert gas; I to IV=individual stirred vessels or bubble columns of a cascade (in FIG. 1a–c represented by way of example by 4 individual apparatus); $A_1$ to $A_{10}$=sub-bubble columns of a cascaded bubble column; $B_1$ to $B_{10}$=trays of a tray column; $C_1$ to $C_{10}$=packing elements or ordered packings of a packed column (A or B or C represented by way of example as 10 apparatus elements in each case); $T^1$=(by way of example) temperature range from 100° to 150° C.; $T^2$=(by way of example) temperature range from 150° to 180° C. (but can be higher); $T^3$=(by way of example) temperature range from 120° to 160° C.; $T^4$=(by way of example) temperature range from 160° to 200° C. (but can be higher), FIG. 1 a with broken lines for the $H_2O$ feed and HCl offtake shows a transverse mode of operation; FIG. 1b with dotted lines for the $H_2O$ feed and HCl offtake shows a cocurrent mode of operation; FIG. 1c with continuous lines for the $H_2O$ feed and HCl offtake shows a countercurrent mode of operation; FIG. 2a shows a cascaded bubble column; FIG. 2b shows a tray column; FIG. 2c shows a packed column. FIG. 3 shows a (for example coiled) reaction tube which can contain internal fittings and mixing elements (not drawn in).

For the purposes of the invention, suppressed backmixing is suppressed mixing of CDOP with the hydrolysed product, i.e. ODOP. Such backmixing should be avoided if possible so that the reaction section can be short and the product remains clean. Backmixing can be avoided by reducing the unhindered flow of starting material and product in the reactor and, by means of separate reactor components, e.g. vessels or bubble columns in a cascade, trays in a column or mixing elements in a tube, giving the reaction mixture a preferred direction towards the outlet of the reactor and allowing transverse flows for the purpose of mixing CDOP and $H_2O$, but no backflow towards the reactor inlet. The abovementioned reactor systems are described in more detail in Ullmann's Encyclopedia 5th Ed. Vol. B4, pp. 181–198 (tube reactors), pp. 275–307 (bubble columns), pp. 321–328 (reaction columns).

EXAMPLE

In a heatable column having a diameter of about 30 mm and a length of about 150 cm, filled with Raschig rings and provided with a heating jacket divided into zones, 586 g (2.50 mol) of CDOP per hour were pumped in at the top and steam at from 150° to 160° C. in an amount of 51 g (2.83 mol) per hour were sent towards the CDOP stream. This stream of steam was divided about equally between two metering-in points, namely about 50 cm and about 100 cm below the top of the column. The column was heated by means of jacket heating using heat-transfer oil, the upper part to from 125° to 135° C., the middle part to from 150° to 160° C. and the lower part to from 170° to 180° C. A nitrogen stream of about 10 l/h entered at the bottom of the column. After the column had been operated for about 2 hours, the product collecting at the bottom, a virtually colourless melt, was drained off continuously and weighed every hour:

| | |
|---|---|
| 1st hour | 549 g |
| 2nd hour | 533 g |
| 3rd hour | 539 g |
| 4th hour | 552 g |
| 5th hour | 531 g; Σ 2704 g, i.e. 12.52 mol of ODOP. |

During this time, a total of 2966 g, i.e. 12.65 mol of CDOP, were metered in. The yield was accordingly about 99% of the theoretical yield. The product obtained (ODOP) had a melting point of from 116 to 117° C., a purity of 99.8% and a chlorine content of from about 70 to 90 ppm. The hydrogen chloride leaving the top of the column was passed through a low-temperature condenser and freed of entrained CDOP which flowed back into the column. A very pure product is obtained at high space-time yields (STY) of from about 0.6 to 0.7 kg of product per l of reaction space and h, which can be increased further.

For comparison:

The procedure of Example 2 of EP 632 050 gives an STY=0.28 kg/l·h and a product having a Cl content of 800 ppm. The procedure of Example 1 of EP 632 050 gives an STY=0.032 kg/l·h.

What is claimed is:
1. A process for preparing a 6-oxo-(6H)-dibenz-[c,e][1,2] -oxaphosphorin (ODOP) of the formula

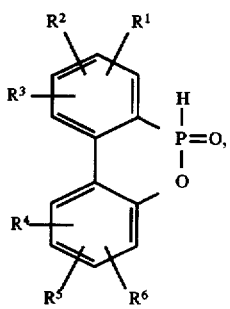

where
R$^1$ to R$^6$ are identical or different and are hydrogen, halogen, C$_1$–C$_4$-alkyl or C$_1$–C$_4$-alkoxy,
by reaction of an o-phenylphenol of the formula

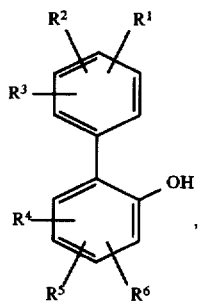

where
R$^1$ to R$^6$ are as defined above,
with phosphorus trichloride in the presence of a Lewis acid with elimination of hydrogen chloride at elevated temperature in the range from 70° to 220° C. in a 1st stage and hydrolysis of the product of the 1st stage in a 2nd stage, wherein, for the purposes of the hydrolysis, ab-chloro-(6H)-dibenz[c,e]-oxaphosphorin and water in an at least stoichiometric molar ratio are fed continuously at elevated temperature into a reaction section having very little backmixing, the hydrolysis is carried out continuously along this reaction section at elevated temperature, the reaction products are discharged continuously at the end of the section and ODOP is optionally subjected to further treatment at elevated temperature.

2. The process of claim 1, wherein the o-phenylphenol used is one in which two of the radicals R$^1$ to R$^6$ are hydrogen.

3. The process of claim 2, wherein the o-phenylphenol used is one in which four of the radicals R$^1$ to R$^6$ are hydrogen.

4. The process of claim 3, wherein unsubstituted o-phenylphenol is used.

5. The process of claim 1, wherein a total amount of H$_2$O of from 1 to 2 mol is used per tool of CDOP.

6. The process of claim 5, wherein a total amount of H$_2$O of from 1 to 1.7 mol is used per mol of CDOP.

7. The process of claim 6, wherein a total amount of H$_2$O of from 1 to 1.5 is used per mol of CDOP.

8. The process of claim 1, wherein the hydrolysis is carded out at a temperature of from 60° to 250° C.

9. The process of claim 8, wherein the hydrolysis is carried out at a temperature of from 80° to 230° C.

10. The process of claim 9, wherein the hydrolysis is carded out at a temperature of from 100° to 220° C.

11. The process of claim 10, wherein the hydrolysis is carried out at a temperature of from 130° to 210° C.

12. The process of claim 1, wherein both stages, but independently of one another, are carded out at pressures of from 0.5 to 50 bar.

13. The process of claim 12, wherein both stages, but independently of one another, are carded out at pressures of from 0.6 to 40 bar.

14. The process of claim 13, wherein both stages, but independently of one another, are carried out at pressures of from 0.8 to 30 bar.

15. The process of claim 1, wherein the finished reaction mixture after separating off HCl is subjected to treatment at elevated temperature in the range from 130° to 250° C.

* * * * *

UNITED STATES PATENT AND TRADEMARK OFFICE
CERTIFICATE OF CORRECTION

PATENT NO. : 5,717,127
DATED : February 10, 1998
INVENTOR(S) : Buysch, et al.

It is certified that error appears in the above-identified patent and that said Letters Patent is hereby corrected as shown below:

| | |
|---|---|
| Col. 7, line 38 | Delete " ab-chloro " and substitute -- a 6-chloro -- |
| Col. 7, line 39 | After " [c,e] " insert -- [1,2] -- ; after " oxaphosphorin " insert --(CDOP) -- |
| Col. 8, claim 5 line 2 | Delete " tool " and substitute -- mol -- |
| Col. 8, line 25 | Delete " carded " and substitute -- carried -- |
| Col. 8, line 29 | Delete " carded " and substitute -- carried -- |
| Col. 8, line 32 | Delete " carded " and substitute -- carried -- |

Signed and Sealed this

Sixth Day of July, 1999

Attest:

Q. TODD DICKINSON

*Attesting Officer*     Acting Commissioner of Patents and Trademarks